United States Patent

Chen et al.

[11] Patent Number: 6,069,477
[45] Date of Patent: May 30, 2000

[54] METHOD FOR IMPROVING THE ACCURACY OF NMR RELAXATION DISTRIBUTION ANALYSIS WITH TWO ECHO TRAINS

[75] Inventors: Songhua Chen, Katy; Daniel T. Georgi, Houston, both of Tex.

[73] Assignee: Western Atlas International, Inc., Houston, Tex.

[21] Appl. No.: 08/994,497

[22] Filed: Dec. 19, 1997

Related U.S. Application Data

[60] Provisional application No. 60/057,981, Sep. 5, 1997.
[51] Int. Cl.$^7$ .................................................. G01V 3/00
[52] U.S. Cl. ........................................................... 324/303
[58] Field of Search ............................................. 324/303

[56] References Cited

U.S. PATENT DOCUMENTS

| | | | |
|---|---|---|---|
| 5,212,447 | 5/1993 | Paltiel | 324/303 |
| 5,557,200 | 9/1996 | Coates | 324/303 |
| 5,936,405 | 8/1999 | Prammer et al. | 324/303 |

OTHER PUBLICATIONS

Chen S., and Georgi T.R., "Improving the accuracy of NMR Relaxation Distribution analysis in Clay–Rich Reservoirs and Core Samples".International Symposium–Society of Core Analysts SCA–9702 pp. 1–10 See figures 4 and 6, Sep. 1997.

*Primary Examiner*—Christine K. Oda
*Assistant Examiner*—Tiffany A. Fetzner
*Attorney, Agent, or Firm*—Karen B. Tripp; Darryl M. Springs

[57] ABSTRACT

The total porosity of a subterranean formation is calculated by summing the effective Porosity and the clay bound water (CBW) porosity. With the invention described in this patent, the distortion effects of clay bound water (CBW) porosity on the measurement of total porosity is filtered out. The effects will be more significant in slialy sand where the CBW porosity component of total porosity is abundant. The correct NMR transverse relaxation time ($T_2$) spectra distribution is essential to a determination of capillary bound fluid (BVI) partial porosity and the Spectral Bulk Volume Irreducible (SBVI) model. The same data correction concept can be applied to make a meaningful comparison of well logs or laboratory core NMR data that are obtained with different interecho time (TE) sampling periods.

15 Claims, 4 Drawing Sheets

STEP 1: INPUT DATA SET A & B
A. NMR $T_2$ LOG DATA (ECHO TRAIN WITH TE=1.2 ms): $A(1.2*j)$
B. NMR CLAY BOUND WATER DATA (ECHO TRAIN WITH TE=0.6 ms, HIGH S/N): $B(0.6*k)$

STEP 2: INVERT DATA SET B WITH MULTIEXPONENTIAL MODEL AND $T_2$ = 0.5, 1, 2, 4, 8, 256 ms. THIS STEP YIELDS PARTIAL POROSITY RESULTS $pp = [pp_{.5}, pp_1, pp_2, pp_4, pp_8, pp_{256}]$

STEP 3: CALCULATE THE EFFECT OF CBW ON $T_2$ LOG (SET A)
$$cor(n) = pp_{0.5} \exp\left(-\frac{n*1.2}{0.5}\right) + pp_1 \exp\left(-\frac{n*1.2}{1}\right) + pp_2 \exp\left(-\frac{n*1.2}{1}\right),$$
$n = 1, \ldots, 12.$ STEP 4: SUBTRACT THE CBW CONTRIBUTION FROM $T_2$ LOG DATA (SET A) FOR THE FIRST 12 ECHOES
$A'(n) = A(n) - cor(n)$, $n = 1, 2, \ldots, 12$ FOR EVERY ECHO TRAIN A
RECONSTRUCT NEW ECHO TRAIN WHICH HAS REMOVED THE CBW EFFECTS:
$A_{NEW}(n) = [A'(1), A'(2), \ldots, A'(12), A(13), \ldots, A(NE)]$
(WHERE "A'(1), A'(2), ...(A')(12)" ARE CORRECTED ECHOES AND "A(13), ...A(NE)" ARE ORIGINAL ECHOES).

STEP 5:
INVERT $A_{NEW}(n)$ TO OBTAIN $T_2$ DISTRIBUTION AND EFFECTIVE POROSITY

STEP 6: COMBINE THE CBW DISTRIBUTION IN STEP 2 AND THE EFFECTIVE POROSITY DISTRIBUTION IN STEP 5 TO OBTAIN TOTAL POROSITY

NE IS THE TOTAL NUMBER OF ECHOES IN A

*Fig. 3*

METHOD FOR IMPROVING THE ACCURACY OF NMR RELAXATION DISTRIBUTION ANALYSIS WITH TWO ECHO TRAINS

RELATED PATENT APPLICATION

This application claims the benefit of prior filed copending U.S. Provisional Application Ser. No. 60/057981, filed Sep. 5, 1997, entitled METHOD FOR IMPROVING THE ACCURACY OF NMR RELAXATION DISTRIBUTION ANALYSIS WITH TWO ECHO TRAINS.

BACKGROUND OF THE INVENTION

1. Field of the Invention

This invention is related to methods for collecting and processing nuclear magnetic resonance (NMR) transverse relaxation time ($T_2$) spectra. In one application, the invention is related to methods for determining porosity measurement of a subterranean formation, or cores from such formation, using NMR tools or instruments.

2. Description of the Related Art

Nuclear magnetic resonance is used in the oil industry, among others, and particularly in certain oil well logging tools. NMR instruments may be used for determining, among other things, the fractional volume of pore space and the fractional volume of mobile fluid filling the pore space of earth formations. Methods of using NMR measurements for determining the functional volume of pore space and the fractional volume of mobile fluids are described, for example, in "Spin Echo Magnetic Resonance Logging: Porosity and Free Fluid Index Determination," M. N. Miller et al., Society of Petroleum Engineers paper no. 20561, Richardson, Tex., 1990. Further description is provided in U.S. Pat. No. 5,585,720, of Carl M. Edwards, issued Dec. 17, 1996, and assigned to Western Atlas International, Inc., entitled "Signal Processing Method For Multiexponentially Decaying Signals And Applications To Nuclear Magnetic Resonance Well Logging Tools." The disclosure of that patent is incorporated herein by reference.

Deriving accurate transverse relaxation time ($T_2$) relaxation spectra from nuclear magnetic resonance (NMR) data from logging subterranean formations, or from cores from such formations, is critical to determining total and effective porosities, irreducible water saturations, and permeabilities of the formations. Accurate spectra are also essential to estimate $T_2$ cutoff values and to obtain coefficients for the film model or Spectral Bulk Volume Irreducible (SBVI) model. Effective porosities are typically summations of partial porosities; however, distortion of partial porosity distributions has been commonly observed for a variety of reasons.

The most common NMR log acquisition and core measurement method employs $T_2$ measurements using CPMG [Carr, Purcell, Meiboom and Gill] sequence, as taught by Meiboom and Gill in "Modified Spin-Echo Method for Measuring Nuclear Relaxation Time," Rev. Sci. Instrum. 1958, 29, pp. 688–691. In this method, the echo data in any given echo train are collected at a fixed time interval, the interecho time (TE). Usually, a few hundred to a few thousand echoes are acquired to sample relaxation decay.

Interecho time (TE), is one of the most important, controllable experimental parameters for CPMG measurements and can affect data interpretation. In logging operations using the MRIL® tool (made by Numar Corp.), TEs of 0.6 and 1.2 milliseconds (ms) are typically used to manipulate the relaxation decay data to include or exclude clay bound water (CBW) porosity. Not all clay bound water has a $T_2$ relaxation time less than 4 ms and not all clay bound water may be resolved with a TE of 0.6 ms. For the purpose of this application, however, NMR $T_2$ relaxation data with $T_2 \leq 2.83$ ms resolved with a TE of 0.6 ms will be referred to as CBW. It will be noted that other values of $T_2$ and TE may be observed with other logging tools.

Both effective and total porosity, the latter defined as the sum of CBW and effective porosity, may be obtained with two CPMG measurements, as taught by Prammer et al in "Measurements of Clay-Bound Water and Total Porosity by Magnetic Resonance Logging," SPE paper 36522, presented at SPE Annual Tech. Conf. and Exhib., Denver, Co., 1996, pp. 311–320. This method implicitly assumes effective porosity, calculated from a TE of 1.2 ms acquisition, and effectively excludes the CBW porosity. This assumption is generally valid for rocks that contain little clay. However, with clay-rich rocks, a further correction may be required to improve the accuracy of the estimated effective porosity.

Interpretation of NMR core or log data is often started by inverting the time-domain CPMG echo decay into a $T_2$-parameter-domain distribution. In general, the $T_2$ of fluids in porous rocks depends on the pore-size distribution and the type and number of fluids saturating the pore system. Because of the heterogeneous nature of porous media, $T_2$ decays exhibit a multiexponential behavior. The basic equation describing the transverse relaxation of magnetization in fluid saturated porous media is $$M(t) = \int_{T_{2\min}}^{T_{2\max}} P(T_2) \exp\left(-\frac{t}{T_2}\right) dT_2, \tag{1}$$

where M is magnetization, and effects of diffusion in the presence of a magnetic field gradient have not been taken into consideration and generally are negligible for short TE. In CPMG measurements, the magnetization decay is recorded (sampled) at a fixed period, TE; thus, a finite number of echoes are obtained at equally spaced time intervals, t=nTE, where n is the index for the $n^{th}$ echo, $$M^{\exp}(nTE) = \int_{T_{2\min}}^{T_{2\max}} P(T_2) \exp\left(\frac{nTE}{T_2}\right) dT_2 + noise \tag{2}$$

Equation (2) follows from Eq. (1) when noise and finite sampling are introduced. Because of the finite sampling of a continuous decay curve, information between the samples is not available. In order to estimate the unknown relaxation distribution function $P(T_2)$, a common approach is to use a set of predetermined relaxation times, $T_2$, and to solve for the partial porosities, ppi, to fit the observed amplitudes, M(nTE). Using this approximation, the relaxation decay curve is modeled by the exponential equation $$M(nTE) = \sum_{i=1}^{k} pp_i \exp\left(\frac{-t}{T_{2i}}\right) \tag{3}$$

which expands to $$M(nTE) = \tag{4}$$

-continued $$pp_1 \exp\left[-\frac{nTE}{T_{2_1}}\right] + pp_2 \exp\left[-\frac{nTE}{T_{2_2}}\right] + \ldots + pp_k \exp\left[-\frac{nTE}{T_{2_k}}\right]$$

where k is the index in the summation.

Mathematically, the multiexponential function is considered a valid approximation in that the function is linearly independent over distinct sampling points, as discussed by Hamming in Numerical Methods for Scientists and Engineers, $2^{nd}$ Edition, McGraw-Hill, N.Y., 1973, pp. 617–619. This property guarantees that a unique and exact solution can be found provided that there is no noise and that a sufficient number of the fitting bins, $T_{2k}$, are used to span all relaxation components in the underlying echo train. However, such strict conditions are not met in typical core and log NMR measurements. Consequently, the quality of the approximate solution is limited. Even small noise disturbances may substantially alter the solution. Generally, the presence of noise degrades the accuracy of $T_2$ spectrum estimation for any $T_2$ distribution patterns, but the short relaxation time components are the most affected. Furthermore, the individual exponential function, $\exp(-t/T_2)$ is non-orthogonal. Thus, even without noise, depending on the fitting model bin selections, signals corresponding to short $T_2$ components could be numerically determined as corresponding to other $T_2$ components.

Inverting time domain NMR echo train data to $T_2$ distributions with the multiexponential relaxation model of equation 4 above is known to be an ill-conditioned problem, particularly since signal-to-noise levels are usually poor for NMR log data. The individual relaxation components in this model are not orthogonal to each other, which makes the estimation very vulnerable to noise. Often, a regularization technique is used to stabilize the results, which has a side effect of introducing artificial smoothing.

NMR relaxation decay is characterized with exponentials. Fourier transform (FT) of the time domain series can be used to analyze the frequency content of an exponential function. The frequency content of the multiexponential decay is the linear superposition of the FT of the individual exponentials. The FT of the continuous time-domain signal of a single exponential decay is $$F.T.[M(t)] = F.T.\left[\exp\left(\frac{t}{T_2}\right)\right] = \frac{T_2(1 - i2\pi f T_2)}{1 + (2\pi f T_2)} \quad (5)$$

which is peaked at zero frequency and the tail depends on the decay constant $T_2$. The discrete FT (DFT) of a single exponential decay echo $$X(k) = DFT[M(t_n)] = DFT\left[\exp\left(\frac{t_n}{T_2}\right)\right], \quad (6)$$

yields the frequency content and the spectrum density $|X(k)|^2/N$, where N refers to length of the DFT and usually equals the number of data samples.

FIG. 1 shows the frequency contents and the spectral density of a single exponential decay with $T_2=1$ ms and several sampling times, TE=0.3, 0.6, 1.2, 2.4, and 4.8 ms, respectively. No noise is added. The number of echoes in each echo train is set to be different so that $TE_i \cdot N_i=512$ msec for this simulation. Distortion of frequency content may occur with inadequate sampling.

FIG. 2 shows that long $T_2$ components have more energy in the low frequency region. Short $T_2$ components have relatively flat power spectra and lack distinctive frequency characteristics. Certain information is lost when $T_2$ is not much larger than TE. Since the frequency contents of different exponential components overlap, the distortion of signal will affect several exponential components, not just the shortest one.

NMR effective porosity (MPHE) is often interpreted to be the summation of the capillary bound fluid as represented by the bulk volume or reducible (BVI) component and movable fluid as represented by the bulk volume movable (BVM) component but clay bound porosity (CBW) is not included. Conventionally NMR effective porosity (MPHE) is calculated as the summation of the partial porosities, i.e.:

$$MPHE = \sum_{j=1}^{k} pp_{T_{2j}} \quad (7)$$

where the summation in the equation includes all partial porosities with $T_2 \geq 4$ ms.

Generally, clay bound water (CBW) relaxes with $T_2 \leq 2$ ms. Since the standard NMR $T_2$ log with, for example, the MRIL® tool of Numar Corp. uses the sampling period TE=1.2 msec, the CBW still can contribute to the NMR $T_2$ log data. These signals often shift to adjacent, later $T_2$ bins, contributing to inaccuracies in effective porosity and bulk-volume irreducible (BVI) estimates. Other tools may use different sampling periods, but the results would likely be similar.

In summary, noise, sampling rate, and the ill-conditioning of inversion and regularization contribute to smearing of the estimated $T_2$ distribution and the shifting of the CBW signal to the higher $T_2$ regions. This distortion is not easily rectified; even adding more bins with short $T_2$ does not reduce the distortion of the $T_2$ spectra. Our invention is a method for properly accounting for and correcting the CBW effect. The principles of the invention are also applicable in correcting other distortions of an NMR echo train.

SUMMARY OF INVENTION

A formation core, or the like typically has many components with many different pore sizes which for analytical purposes are classified into groups of sizes. The pores in each group are assumed to have the same average size. These groups are chosen to possess a series of $T_2$ values, as for example $T_{2i}=0.5$ ms, 1 ms, 2 ms, 4 ms, 8 ms, and 256 ms. Each such $T_{2i}$, in turn, is assumed to reflect a partial porosity of the total porosity. In that regard, certain rock components such as clay bound water (CBW) appear to possess a porosity which is preferably discarded in determining partial porosities. It is a feature of the invention to filter out the distorting component of CBW apparent porosity from the measurement of MPHE.

The effective porosity of a subterranean formation or core from such formation, as indicated by NMR data, may be overestimated and is TE dependent if the core or formation has fast $T_2$ relaxing components, such as, for example, clay bound water. The degree of misinterpretation depends on several factors, such as the quantity of CBW, mean $T_2$, and signal-to-noise ratio (SNR). Since the systematic error is difficult to correct by simply subtracting in the $T_2$ domain, a time-domain correction procedure is applied before inversion. The essence of the correction is to filter out the contribution of the fast $T_2$ relaxing components such as CBW in the 1.2 TE echo train. For example, TCBW=2.83 ms may be used as the $T_2$ cutoff between CBW and BVI, which is the midpoint in log scale between the last CBW $T_2$ bin (2 ms) and the first BVI bin (4ms).

The new method described uses the partial porosity distributions obtained from NMR echo data. High S/N echo data with sampling time TE=0.6 ms are used to obtain the CBW $T_2$ distribution. These data are then used to reconstruct CBW contributions to the time domain early echoes of the conventional effective porosity echo data (TE=1.2 ms). The CBW signal is then subtracted from the original echoes, and the effective porosity distribution is estimated from the reconstructed echo train.

BRIEF DESCRIPTION OF THE DRAWINGS

FIG. 3 is a flow chart of steps of the invention.

DESCRIPTION OF THE PREFERRED EMBODIMENT

Figure 1:
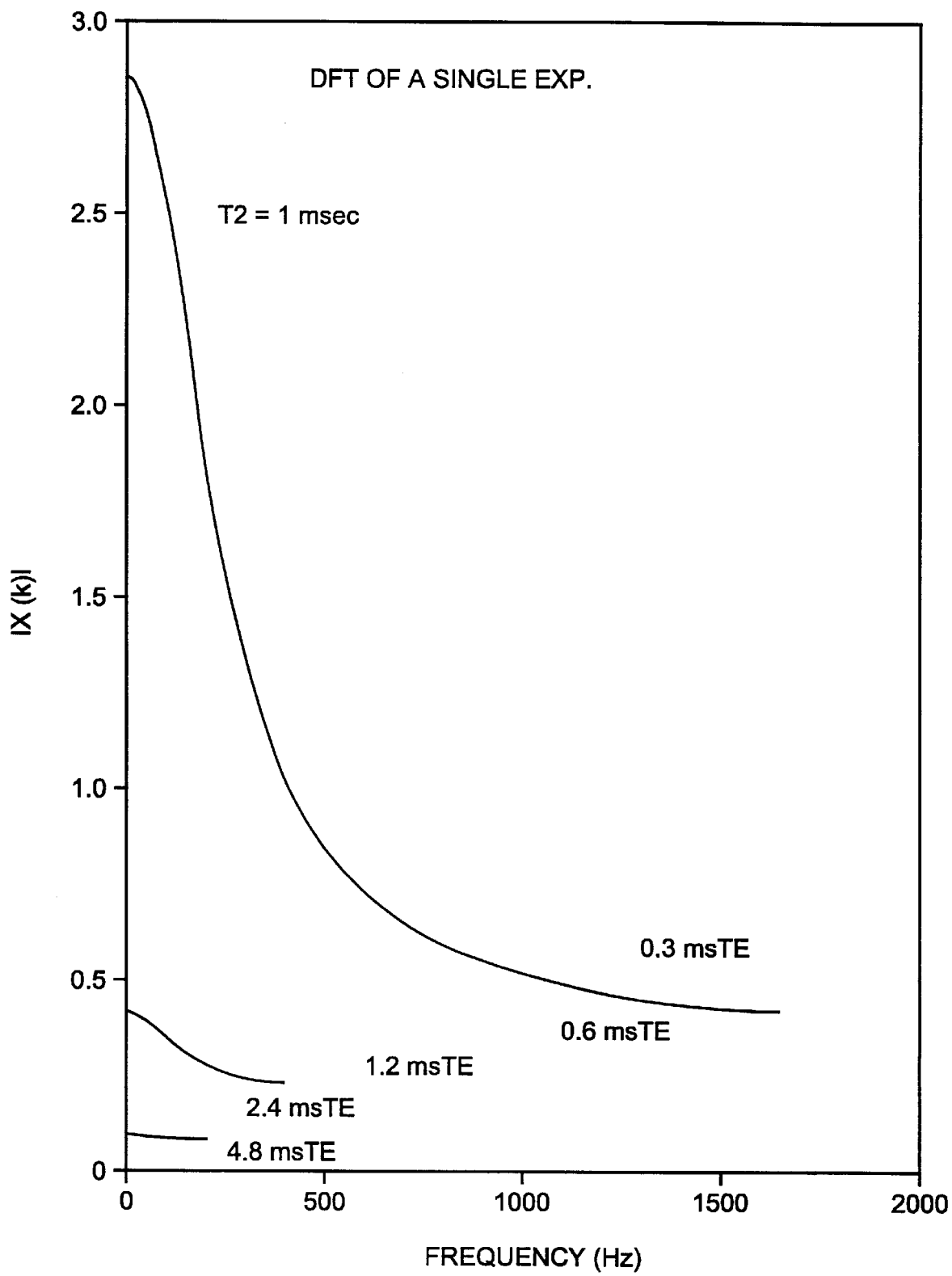
FIG. 1 is a graph showing the frequency contents and spectral density of a single exponential decay with $T_2$=1 ms and several sampling times.
Figure 2:
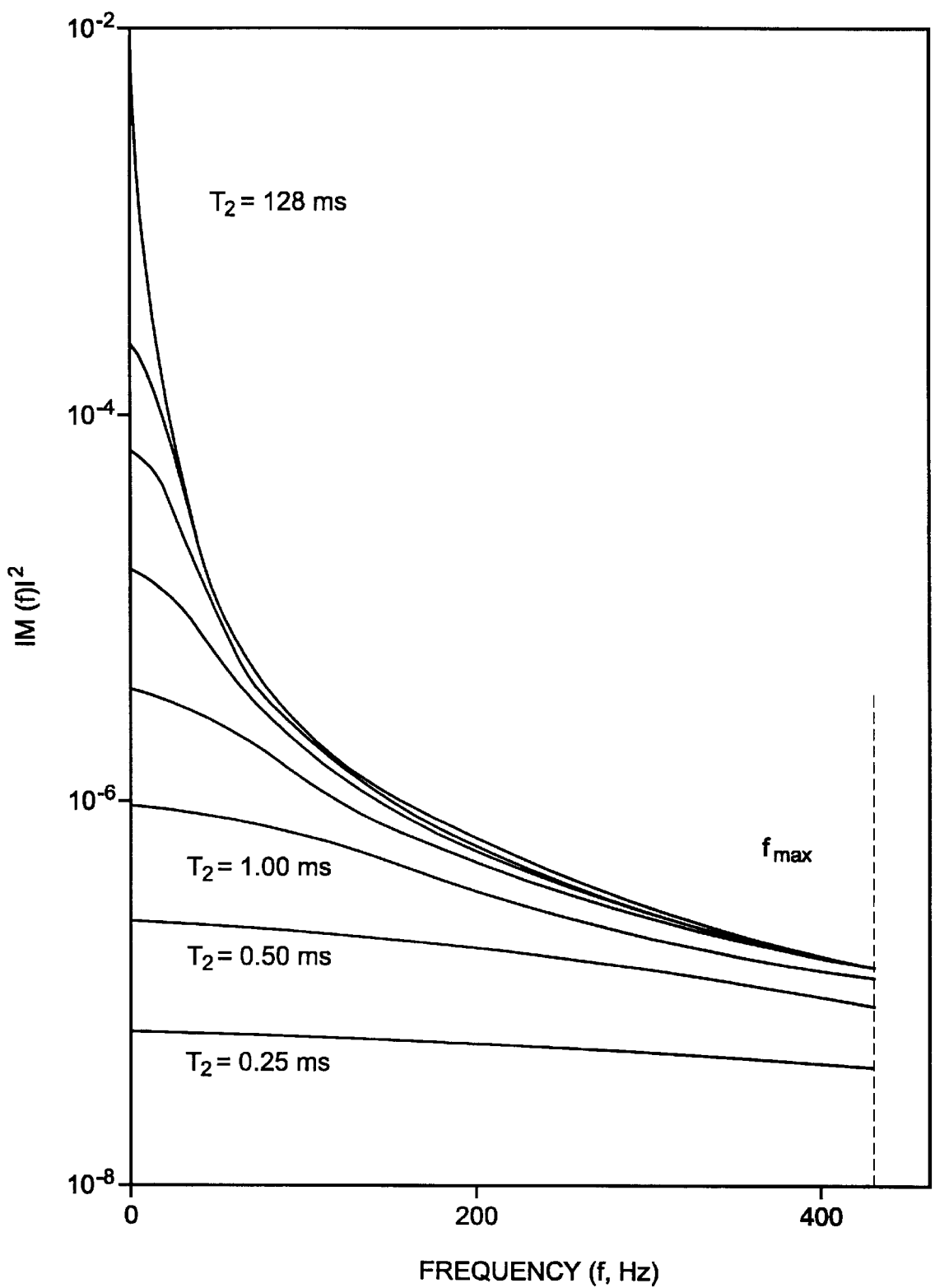
FIG. 2 is a plot of power spectra from zero to $f_{max}$ of exponentials with different $T_2$ constants.

An inadequate sampling rate, due to the tool performance limitations used to acquire relaxation decay data can affect the calculated relaxation distribution, particularly the short relaxation components. Adverse effects in the data analysis with an inadequate TE are often observed for noisy data. This problem can be eased if the signal to noise ratio is adequately improved, as the spectral resolvability depends on SNR$\sqrt{TE}$. Without noise, it is possible to recover $T_2$ components even for $T_2$ as short as $T_2$=TE15 with an adequate inversion technique. Thus, improving the signal to noise ratio is key to improving recoverability.

According to sampling theory, for a given sampling period, TE, the maximum frequency that can be recovered is $$f_{max} = \frac{1}{2TE} \quad (8)$$

Furthermore, for a record length of T=NE.TE, where NE is the total number of echoes in the CPMG measurement, the frequency resolution is $$\Delta f = 1/T \quad (9)$$

Since two different echo series may have different numbers of echoes and TEs, their frequency contents may be different because of different frequency resolution and $f_{max}$. Thus, it is possible that one echo series is more sensitive to one type of frequency content than the other, even for measurements done in the same sensitive volume.

Typical NMR instrument noise is white, containing all frequencies. Since the frequency content of the short $T_2$ component is quite flat, i.e., contains all frequencies, it is the most vulnerable to the effects of the random noise. An echo series having a relatively short record length has poorer frequency resolution resulting in reduced resolvability in a long $T_2$ region. On the other hand, an echo train with a long record period and long TE has good frequency resolution, but if truncated at high frequencies is more easily distorted with the fast $T_2$ components. Properly combining the two spectra can yield a complete spectrum with improved accuracy.

In this invention, the CBW contribution is filtered out of the effective $T_2$ distribution and effective porosity. The effective $T_2$ distribution is defined as the transverse $T_2$ distribution greater than or equal to about 2.83 ms and the effective porosity is defined as the sum of the partial porosities corresponding to $T_2$=about 2.83 ms and above. The clay bound water porosity, on the other hand, refers to the porosity distribution corresponding to $T_2$<about 2.83 msec.

The clay bound water porosity is logged with the MRIL® C/TP tool by operating with a sampling period of TE=0.6 msec (labeled Data set B in FIG. 3). Typically, 50 repeat acquisitions of 10 echoes are obtained at each depth with this mode and a single echo train of several hundred echoes is acquired with a TE of 1.2 ms for the effective porosity. Thus, the signal to noise ratio (SNR) is approximately 7 times better with CBW echo data than the echo data for an effective porosity log. The wait time (e.g., 20 ms) in CBW logs is considerably shorter than the wait time used for more fully polarized $T_2$ log acquisitions. Consequently, $T_2$ components corresponding to CBW are fully polarized; longer components are only partially polarized.

The CBW porosity distribution is obtained by inverting these echoes with a multiexponential distribution model, such as that of equation 3, or with, for example, six bins ($T_{2i}$ of 0.5, 1, 2, 4, 8, 256 ms). The sum of the first three bins is the CBW porosity. The last three bins are used to account for partially recovered porosities and are discarded (see Steps 1 and 2 in FIG. 3). Because SNR is high, the CBW can be estimated relatively accurately.

The CBW porosity contributes partly to the echo train acquired with sampling period TE=1.2 msec (labeled Data set A in FIG. 3). This contribution must be removed. In order to remove the contribution of clay bound water porosity from the regular 1.2 ms TE echo train (labeled Data set A in FIG. 3), the forward calculation of the CBW echo decay contribution is performed using the three CBW bin partial porosities (as described in step 3 in FIG. 3). CBW has little effect on the echo signals beyond 5 times its highest $T_2$ component (i.e., 5×2.83 msec=14.15 msec ). Thus, the forward modeling of the CBW echo decay signal is only needed for echo 1 to echo 12 in this example. The constructed CBW echo decay amplitudes are subtracted from the corresponding echo amplitudes in the Data set A echo train (See Step 4). The corrected echo train is reconstructed with the 12 new echo amplitudes plus the remainder of the original echo amplitudes in set A. The corrected echo train is, therefore, not contaminated by CBW porosities. Finally, the effective $T_2$ distribution and effective porosity are calculated by inverting the reconstructed echo train.

These corrections are only necessary for zones with CBW. When the CBW approaches zero the correction approaches zero and the subtraction does not alter the original data. The accuracy of the correction is related to the SNR of the 0.6 ms TE echo train data. In a simulation with 500 sets of synthetic data with SNR=60, for example, the estimated CBW values using the method described in step 2 of FIG. 3 has an 80% confidence interval within ±10% accuracy of the model CBW value. Increasing the number of echoes (TE=0.6 MS) does not appear to improve CBW estimate accuracy, which is consistent with there not being much CBW information carried beyond about the 10$^{th}$ echo.

Figure 4:
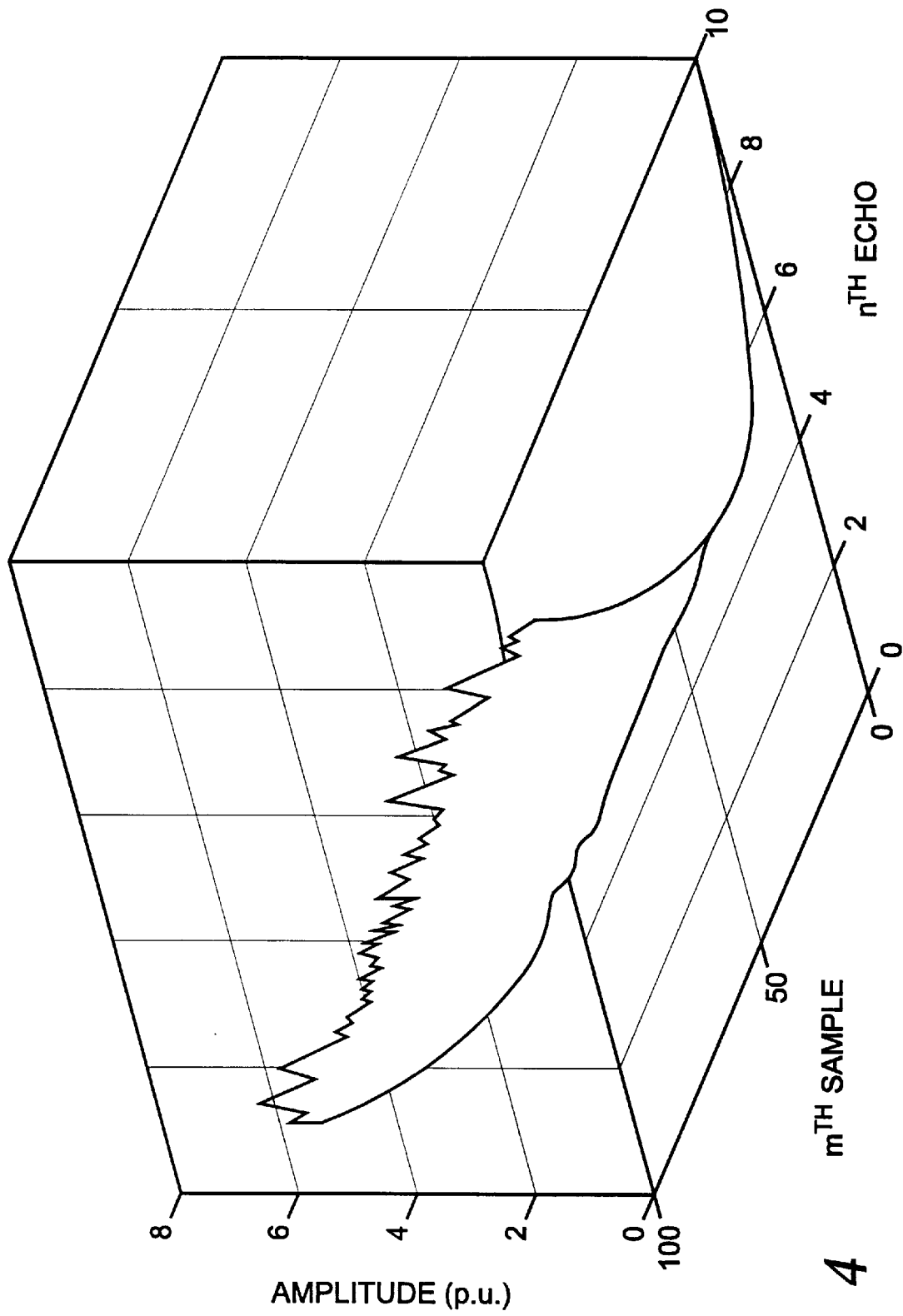
FIG. 4 is a graph showing data reconstructed according to the method of this invention.

Furthermore, although the individual CBW components may have larger error bars, the collective contribution of the CBW bin partial porosities substantially improved the signal to noise ratio, as has been shown in FIG. 4 and Table 1 below.

TABLE 1

| S/N | CBW input | estimated mean CBW | std. dev |
|-----|-----------|--------------------|----------|
| 100 | 10        | 10.18              | 0.73     |
| 50  | 10        | 10.09              | 1.07     |
| 10  | 10        | 10.16              | 2.10     |

The principle of the invention and the best mode contemplated for applying that principle have been described. It is to be understood that the foregoing is illustrative only and that other means and techniques can be employed without departing from the true scope of the invention defined in the following claims.

We claim:

1. A method for collecting and processing nuclear magnetic resonance transverse relaxation time data comprising:
    a. collecting at least two echo trains wherein the interecho time for the first echo train is greater than or equal to the interecho time for the second echo train and the number of echoes in the first echo train is greater than the number of echoes in the second echo train; and
    b. correcting distortion of the first echo train by using decay information derived from the second echo train.

2. A method for determining the effective porosity of a subterranean formation comprising:
    a. logging the subterranean formation with a logging tool using nuclear magnetic resonance;
    b. collecting nuclear magnetic resonance echo data during said logging, including collecting at least two echo trains wherein the interecho time for the first echo train is greater than or equal to the interecho time for the second echo train and the number of echoes in the first echo train is greater than the number of echoes in the second echo train;
    c. filtering out the contribution of the clay bound water to the echo data acquired with the interecho time for the first echo train, using decay information derived from the echo train recorded with the interecho time for the second echo train; and
    d. calculating the effective porosity of the formation.

3. The method of claim 2 wherein acquisitions of echoes are obtained at about 0.6 ms for the second echo train and at about 1.2 ms for the first echo train.

4. The method of claim 2 wherein such logging with multiple echo trains is conducted at depths in the formation having clay bound water.

5. The method of claim 2 wherein the contribution of the clay bound water to the echo data is determined by inverting the echoes taken at the shorter interecho times with a relaxation distribution model.

6. The method of claim 5 wherein the model is a multiexponential distribution model.

7. The method of claim 3 wherein the filtering out of the contribution of the clay bound water is obtained by forward modeling the clay bound water contribution to the longer interecho time-domain echo signals and subtracting the clay bound water contribution from the echo data taken at about 1.2 ms for about the first 12 data for each logging depth for which data was taken.

8. A method for determining the effective porosity of a subterranean formation having clay bound water comprising
    (a) logging said formation with nuclear magnetic resonance and collecting transverse relaxation time log data from an echo train at two interecho intervals, one longer than the other;
    (b) inverting said data collected at the shorter interecho time interval to obtain the effects of clay bound water of the partial porosity of said formation;
    (c) calculating the effect of clay bound water on the transverse relaxation time log data collected at the longer interval;
    (d) subtracting the contribution of the clay bound water from the data collected at the longer interval for about the first 12 echoes;
    (e) reconstructing a new echo train from the data collected at the longer interval which has the clay bound water effects removed; and
    (f) inverting the new echo train to obtain a transverse relaxation time log data distribution and effective porosity of the formation.

9. The method of claim 8 further comprising combining the partial porosity of step (b) and the effective porosity of step (f) to obtain total porosity.

10. The method of claim 8 wherein said transverse relaxation time log data is inverted according to step (b) with a multiexponential model.

11. The method of claim 8 where the effect of the clay bound water is calculated according to step (c) using the formula $$cor(n) = pp_{0.5}\exp\left(-\frac{n \cdot 1.2}{0.5}\right) + pp_1\exp\left(-\frac{n \cdot 1.2}{1}\right) + pp_2\exp\left(-\frac{n \cdot 1.2}{2}\right),$$

where n is chosen to be from the first echo to the $n^{th}$ at which all CBW signal is decayed.

12. A method of nuclear magnetic resonance logging which includes correcting the transverse ($T_2$) relaxation spectrum of a substance for a distorting component having a relatively short decay time, which comprises:
    (a) collecting a first echo train from the substance at a first interecho time ($TE_1$);
    (b) collecting a second echo train from the substance at about the same time and position as the first echo train, and additionally at a second interecho time ($TE_2$), where the number of echoes is chosen to resolve the distorting component; and
    (c) correcting the first echo train for distortion derived from the second echo train.

13. The method defined in claim 12, wherein the substance is a subterranean formation containing clay bound water, $TE_1$ is about 1.2 ms, and $TE_2$ is about 0.6 ms.

14. The method defined in claim 12 wherein the first echo train includes about 100 to 500 echoes and the second echo train comprises a stack of echo trains each having about 5 to 15 echoes.

15. The method as defined in claim 12, wherein the correction of the first echo train includes inverting the second echo train and best fitting the data of the second train to a relaxation distribution.

* * * * *